United States Patent [19]

(12) United States Patent
Sem

(10) Patent No.: US 8,927,291 B2
(45) Date of Patent: Jan. 6, 2015

(54) METHODS FOR DETECTING DITHIO-CONTAINING PROTEINS USING QUENCHED FLUOROPHORES CONJUGATED TO PEPTIDES VIA LINKERS CONTAINING DITHIO GROUPS

(71) Applicant: Marquette University, Milwaukee, WI (US)

(72) Inventor: Daniel S. Sem, New Berlin, WI (US)

(73) Assignee: Marquette University, Milwaukee, WI (US)

( * ) Notice: Subject to any disclaimer, the term of this patent is extended or adjusted under 35 U.S.C. 154(b) by 0 days.

(21) Appl. No.: 13/665,478

(22) Filed: Oct. 31, 2012

(65) Prior Publication Data

US 2013/0122600 A1     May 16, 2013

Related U.S. Application Data

(62) Division of application No. 12/816,125, filed on Jun. 15, 2010, now abandoned.

(60) Provisional application No. 61/268,688, filed on Jun. 15, 2009.

(51) Int. Cl.
| | |
|---|---|
| *G01N 21/64* | (2006.01) |
| *C07C 323/35* | (2006.01) |
| *C07C 323/52* | (2006.01) |
| *C07K 5/02* | (2006.01) |
| *G01N 33/58* | (2006.01) |
| *G01N 33/68* | (2006.01) |

(52) U.S. Cl.
CPC .......... *G01N 21/6428* (2013.01); *C07C 323/35* (2013.01); *C07C 323/52* (2013.01); *C07K 5/02* (2013.01); *G01N 33/582* (2013.01); *G01N 33/6842* (2013.01); *C12N 2740/16311* (2013.01)
USPC .............. 436/86; 436/120; 436/172; 530/408

(58) Field of Classification Search
None
See application file for complete search history.

(56) References Cited

U.S. PATENT DOCUMENTS

| | | |
|---|---|---|
| 6,750,357 B1 | 6/2004 | Chiarello et al. |
| 2002/0012947 A1 | 1/2002 | Bevers et al. |
| 2007/0054410 A1 | 3/2007 | Sem et al. |

OTHER PUBLICATIONS

Piggott, A. M. et al. "Fluorometric Assay for the Determination of Glutathione Reductase Activity," Anal. Chem. 2007, 79, 8769-8773.*
Friedler et al., "Development of a functional backbone cyclic mimetic of the HIV-1 tat arginine-rich motif", J. Biol. Chem., 2000, 275:23783-23789.
Pullela et al., "Fluorescence-based detection of thiols in vitro and in vivo using dithiol probes", Analytical Biochemistry, 2006, 352:265-273.
International Search Report for PCT/US2010/038688, dated Mar. 28, 2011.
Written Opinion for PCT/US2010/038688, dated Mar. 28, 2011.
International Preliminary Report on Patentability for PCT/US2010/038688, dated Dec. 29, 2012.

* cited by examiner

*Primary Examiner* — Yelena G Gakh
*Assistant Examiner* — Michelle Adams
(74) *Attorney, Agent, or Firm* — Andrus Intellectual Property Law, LLP

(57) ABSTRACT

Disclosed are dithio compounds that include a quenched fluorophore and a non-fluorophore peptide linked via a dithio bond to the fluorophore. The dithio compounds may be used in methods for detecting thiol-containing compounds or dithio-containing compounds. The dithio compounds also may be used as cellular probes where the peptide portion of the compounds targets the compounds to a specific cellular location.

2 Claims, 9 Drawing Sheets

METHODS FOR DETECTING DITHIO-CONTAINING PROTEINS USING QUENCHED FLUOROPHORES CONJUGATED TO PEPTIDES VIA LINKERS CONTAINING DITHIO GROUPS

CROSS-REFERENCE TO RELATED APPLICATIONS

The present application is a divisional of U.S. application Ser. No. 12/816,125, filed Jun. 15, 2010, which application was published on Dec. 16, 2010, as U.S. Publication No. 20100317119, and claims the benefit under 35 U.S.C. §119 (e) to U.S. Provisional Application No. 61/268,688, filed on Jun. 15, 2009, the entire contents of which are incorporated herein by reference.

BACKGROUND

The disclosed compounds generally relate to the field of dithio reagents. In particular, the disclosed compounds generally relate to quenched fluorescent dithio reagents that are linked to a peptide via a linker containing a dithio group. The compounds may be useful for detecting thiol-containing compounds and dithio-containing compounds.

Thiols are ubiquitous in cellular biochemistry, playing important roles in determining protein structure (as disulfide linkages) and enzymatic mechanisms (as covalent catalysts). Furthermore, the redox state in the cell is largely regulated by the thiol/disulfide status of glutathione in the cell (i.e., GSH vs GSSG). In addition, reduced glutathione (i.e., the thiol form or GSH) also plays a control role in drug metabolism by attacking electrophilic atoms. Therefore, thiol detection and quantitation is important, in cellular biochemistry, and to date has been accomplished most commonly by performing UV-Visible assays using colon metric reagents such as Ellman's reagent. Recently, new probes and associated methods to detect thiols have also been reported whereby quenched fluorophores are reacted with thiols, thereby leading to a fluorescence signal (e.g., Tang et al. (2007) J. Am. Chem. Soc. 129, 11666; Lin et al. (2009) Chemistry 15, 5096). These methods do not involve use of disulfide probes, especially those tethered to peptides which provide lower background signal relative to other fluorescent disulfide compositions. Furthermore, no probes or methods have been reported to date that permit direct detection of disulfides, especially disulfides inside live cells.

Fluorescence detection systems (e.g., fluorescence spectroscopy) have been widely used to study the structure, mechanism and function of different proteins and enzymes, and especially in enzymatic activity or binding assays. Fluorescence detection systems are useful in that they generally have high sensitivity and a good dynamic range for detection. In addition, many generic fluorescent, reagents are available, as well as commercially available equipment for detecting particular reagents. Fluorescence detection systems may be amenable to high throughput screening (e.g., using any bench-top fluorescence plate reader). Potential drawbacks associated with some fluorescence reagents may include photobleaching, stability, and purity of the utilized fluorophore. Some commercially available fluorescent labeling reagents are mixtures of isomers or have high photobleaching or cause uncontrolled labeling, which prevents them from giving reliable and reproducible results. Some also have background fluorescent signal, and others suffer from having a lack of selectivity for the molecule or functional group (e.g., thiols or disulfides) being detected.

As such, fluorescent dithio reagents are desirable. In particular, fluorescent dithio reagents that are photostable, single isomers are desirable. Further, fluorescent dithio reagents that may be used as cellular probes are desirable.

SUMMARY

Disclosed herein are dithio compounds. The dithio compounds typically include a quenched fluorophore and a non-fluorophore peptide linked via a dithio bond to the fluorophore. The dithio compounds described herein may be used in methods for detecting thiol-containing compounds or dithio-containing compounds. The dithio compounds also may be used as cellular probes where the peptide portion of the compounds targets the compounds to a specific cellular location.

The dithio compounds may have a formula F—S—S—P, where "F" includes a quenched fluorophore and "P" includes a non-fluorophore peptide. The fluorophore typically exhibits dequenching when the dithio bond of the dithio compound is reduced (e.g., upon reaction with a thiol-containing compound) or when the dithio compound reacts with another dithio-containing compound in an exchange reaction. In the compound, the fluorophore may be quenched via an interaction between the fluorophore and a quencher (or a quenching moiety) comprising at least one of the non-fluorophore peptide (P) and the dithio bond of the linker (S—S). In some embodiments, the quencher is capable of increasing or decreasing the absorption (extinction coefficient) for the fluorophore. In other embodiments, the fluorophore is quenched by dynamic quenching. In further embodiments, the fluorophore is quenched by dynamic quenching that occurs by fluorescence resonance energy transfer ("FRET"). In even further embodiments, the fluorophore is quenched by static quenching.

The dithio compounds described herein may have a formula F—$X^1$—S—S—$X^2$—P where $X^1$ and $X^2$ may be the same or different and may include $C_{1-18}$ alkyl groups, alkenyl groups, alkynyl groups, aryl groups and combinations thereof. The fluorophore and the quencher may be present at a selected distance within the compounds (e.g., at a selected linear distance for quenching to occur). For example, the fluorophore and the quencher may be present in the dithio compounds at a distance of about 6-100 angstroms, preferably 15-75 angstroms, more preferably about 30-70 angstroms. In some embodiments, the fluorophore and the quencher may be present in the dithio compounds at a distance of about 3-100 angstroms, preferably 3-75 angstroms, more preferably about 3-50 angstroms. In further embodiments, the fluorophore and the quencher are present in the compound at a distance of no more than about 20 angstroms.

The dithio compounds may include any suitable fluorophore. For example, suitable fluorophores may include a fluorophore selected from a group consisting of fluorescein-type fluorophores, rhodamine-type fluorophores, xanthine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, and lanthanide chelate-type fluorophores.

The dithio compounds include a non-fluorophore peptide linked to the fluorophore via an S—S bond. Suitable non-fluorophore peptides may be aliphatic in nature, for example, lacking aromatic amino acids such as His, Tyr, Phe, and Trp or having a low percentage of aromatic amino acids such as His, Tyr, Phe, and Trp relative to total amino acids (e.g., having less than about 20%, 10%, 5%, 3%, or 1% aromatic amino acids).

Suitable non-fluorophore peptides may exhibit one or more biological functions, which may include, but are not limited to, biological transport or targeting activity. For example, suitable non-fluorophore peptides may facilitate transport or retention of the dithio compound across a cell membrane or cell wall or into a cell organelle.

Dithio compounds that include a linked fluorophore and peptide may be prepared by any suitable method. For example, the dithio compounds may be prepared by reacting precursors that include: (A) a first precursor that includes a fluorophore; (B) a second precursor that includes a peptide; and (C) a dithio reagent having the formula $X^1$—S—S—$X^2$, where $X^1$ and $X^2$ may be the same or different and each includes at least one reactive group capable of reacting with the first precursor and the second precursor. The dithio reagent may comprise diamino diphenyl disulfide and cystamine.

In suitable embodiments of the method for preparing dithio compounds, the first precursor may include a fluorophore selected from the group consisting of fluorescein-type fluorophores, rhodamine-type fluorophores, xanthine-type fluorophores, naphthalene-type fluorophores, carbocyanine-type fluorophores, dipyrromethene boron-type fluorophores, coumarin-type fluorophores, acridine-type fluorophores, pyrene-type fluorophores, DANSYL-type fluorophores, lanthanide chelate-type fluorophores, as well as luciferin, which exhibits luminescence after being acted on by the luciferase enzyme. The second precursor may include a non-fluorophore peptide. In some embodiments, the methods may include reacting precursors that include; (A) a first precursor that includes a fluorophore; (B) a second precursor that includes a non-fluorophore peptide; and (C) a dithio reagent. The dithio reagent typically has a formula $X^1$—S—S—$X^2$, where $X^1$ and $X^2$ may be the same or different and each includes at least one reactive group capable of reacting with the first precursor and the second precursor. In other embodiments, the precursors for preparing the dithio compounds include: (A) a first precursor including a fluorescein-type fluorophore; (B) a second precursor including a non-fluorophore peptide; and (C) a dithio reagent having the formula $X^1$—S—S—$X^2$, where $X^1$ and $X^2$ may be the same or different and each include at least one reactive group capable of reacting with the first precursor and the second precursor. In further embodiments, the precursors for preparing the dithio compounds include: (A) a first precursor including a naphthalene-type fluorophore; (B) a second precursor including a non-fluorophore peptide; and (C) a dithio reagent having the formula $X^1$—S—S—$X^2$, where $X^1$ and $X^2$ may be the same or different and each include at least one reactive group capable of reacting with the first precursor and the second precursor. In even further embodiments, the precursors for preparing the dithio compounds include: (A) a first precursor including a DANSYL-type fluorophore; (B) a second precursor including a non-fluorophore peptide; and (C) a dithio reagent having the formula $X^1$—S—S—$X^2$, where $X^1$ and $X^2$ may be the same or different and each include at least one reactive group capable of reacting with the first precursor and the second precursor.

In some embodiments, the fluorophore may be derivatized to make its fluorescence spectrum pH independent between pH 6 and pH 8. For example, the fluorophore may be halogenated and suitable fluorophores may include a halogenated fluorescein-type fluorophore and a halogenated rhodamine-type fluorophore. In other embodiments, the fluorescein-type fluorophore is a derivative of fluorescein in which the carboxyl group is replaced with any group that cannot cyclize (e.g., an alkyl, haloalkyl, or halo group). In other embodiments, the fluorescein-type fluorophore is a derivative of fluorescein or an analog of fluorescein in which the carboxyl group is linked to the cyclic nitrogen atom of piperazine. In further embodiments, the fluorescein-type fluorophore is a derivative of fluorescein or an analog of fluorescein in which the hydroxyl groups are oxidized to ketones or replaced with alkoxy groups (e.g., methoxy or ethoxy).

In some embodiments of the methods for preparing dithio compounds, the dithio reagent may include reactive groups, (e.g., $X^1$ and $X^2$ each may include at least one amino group) and the first precursor and the second precursor each may include reactive groups (e.g., at least one amine-reactive group). Suitable reactive groups may include amine-reactive groups and carbonyl-reactive groups. Amine-reactive groups may include isothiocyanate groups, carboxyl groups, succinimidyl ester groups, and sulfonyl groups. Carbonyl-reactive groups may include amino groups and hydrazide. Suitable dithio reagents for preparing the dithio compounds may include cystamine and diamino-diphenyl disulfide. Suitable precursors include isothiocyanate-containing fluorophores, sulfonyl-containing fluorophores, carboxyl-containing fluorophores, and the like.

In some embodiments of the method, the first, precursor and the second precursor each may include at least one amine-reactive group and the dithio reagent has a formula $X^1$—S—S—$X^2$, where $X^1$ has the formula —$X^1$—$NH_2$; $X^2$ has the formula —$X^4$—$NH_2$; $X^3$ and $X^4$ may be the same or different and include groups independently selected from the groups consisting of $C_{1-18}$ alkyl groups, alkenyl groups, alkynyl groups, and groups and combinations thereof. In some embodiments $X^3$ and $X^1$ may be the same or different and include and groups. The dithio compounds described herein (and which may be prepared by the method) may have a formula F—$X^3$—S—S—$X^4$—P, where "F" includes a fluorophore and "P" includes a peptide. $X^3$ and $X^4$ may be the same or different and may include aryl groups.

Also disclosed herein are methods for detecting thiol-containing compounds and/or dithio-containing compounds. In some embodiments the methods include (A) reacting a reaction mixture to form at least one reaction product; and (B) detecting the at least one reaction product. Typically, the reaction mixture will include (i) the thiol-containing compound and/or the dithio-containing compound; and (ii) a fluorescent dithio compound as described herein. For example, suitable fluorescent dithio compounds for the detection methods include dithio compounds having a formula F—S—S—P, in which "F" includes a fluorophore and "P" includes a non-fluorophore peptide. In the methods for detecting thiol-containing compounds and/or dithio-containing compounds as described herein, detecting the at least one reaction product may include observing dequenching of the fluorophore. Detecting the at least one reaction product may also include measuring an increase or decrease in the absorbance spectrum for the fluorophore.

The methods may be used to detect any suitable thiol-containing compound or dithio-containing compounds. For example, the methods may be used to detect thiol-containing compounds such glutathione, mycothiol, homocysteine, cysteine-containing peptides or proteins, ADPβS, GDPβS, and combinations thereof. The methods may be used to detect altered levels of thiols and/or dithios in cell walls or membranes, such as in bacterial cell walls or in the chorion of embryos. Such dithios may include those in oxidized membrane-bound or membrane-associated proteins such as the *E. coli* Dsb system, and its eukaryotic homologs, as well as lipid transport proteins like as apoE and lipovitellin, cytokines, and C-reactive proteins (CRP). The methods may be used to detect thiols and/or dithios quantitatively, as in clinical or biochemical assays, or qualitatively, as in a histological stain for tissue samples.

The method may be used to detect thiol-containing compounds having a formula X—S—H, where the at least one reaction product has a formula selected from F—S—S—X, P—S—S—X, F—S—H, P—S—H, and salts thereof. Detecting the at least one reaction product may include detecting dequenched fluorescence or altered absorbance of the fluorophore in a reaction product having a formula selected from D-S—S—X, D-S—H, and salts thereof. The method may be used to detect dithio-containing compounds having a formula X—S—S—X, wherein the at least one reaction product has a formula F—S—S—X (i.e., a mixed disulfide) and salts thereof. Suitable thiol- and dithio-containing compounds may include polypeptides or proteins.

The methods for defecting thiol-containing compounds and/or dithio-containing compounds as described herein may be performed continuously or in real-time. The methods for detecting thiol-containing compounds and/or dithio-containing compounds may be performed in vitro, in vivo, and/or in situ.

DETAILED DESCRIPTION

Figure 1:
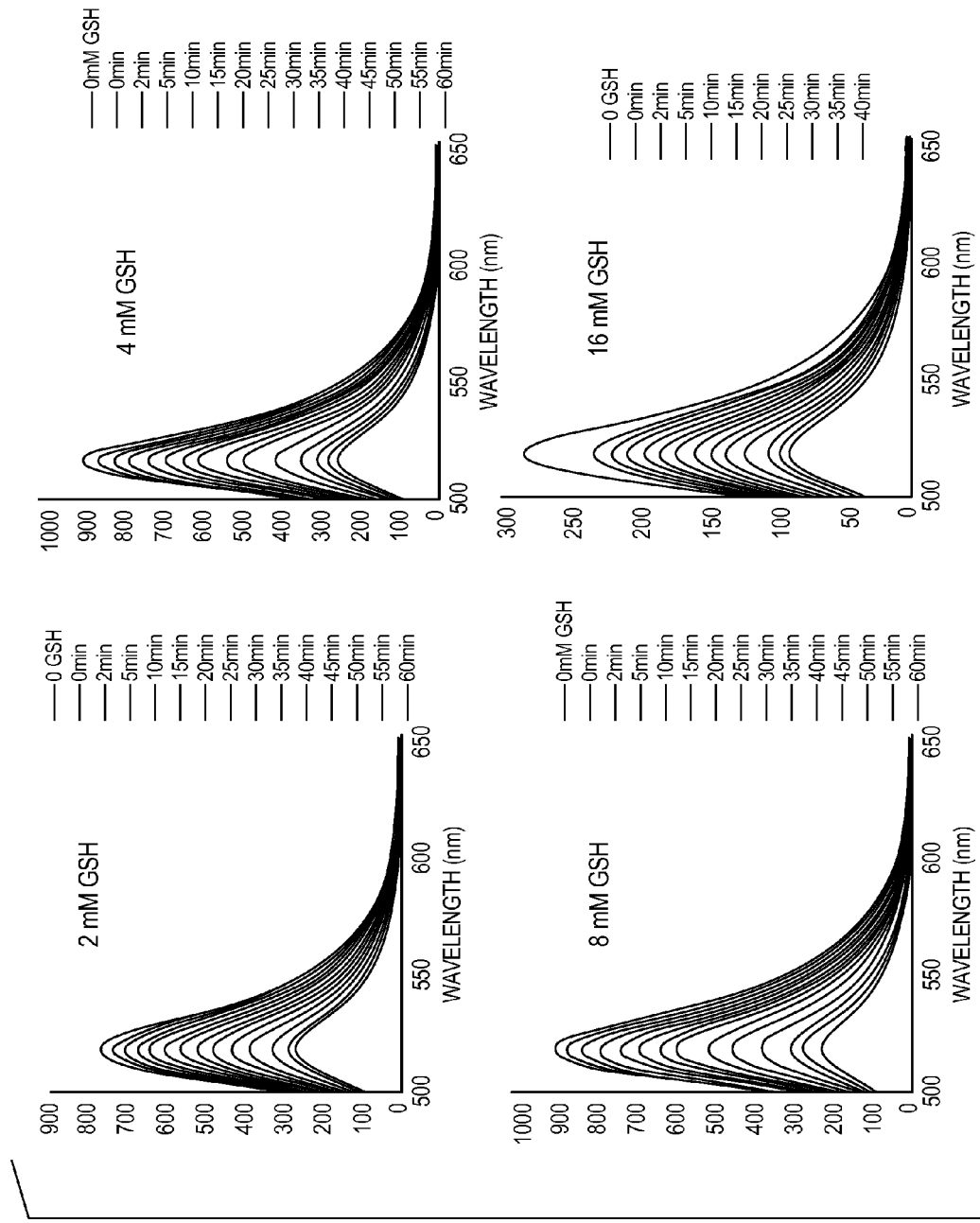
FIG. 1. illustrates that the reaction of a dithio compound and G-S—H exhibits a rapid decrease in fluorescence first, due to formation of the F—$X^1$—S—S-glutathione intermediate, before increasing.

Disclosed herein are dithio compounds. The dithio compounds described herein may be used in methods for detecting thiol- and other dithio-containing compounds. For example, the dithio compounds may be reacted with thiol- or other dithio-containing compounds to detect the thiol- or other dithio-containing compounds.

As used herein, "dithio" means the chemical group —S—S—. A "dithio compound" is a compound that includes at least one chemical group —S—S—. As used herein, "dithio" is interchangeable with "disulfide."

As used herein, "thiol" means the chemical group —S—H or the ionized form of —S—H, i.e., —S—. A "thiol-containing compound" is a compound that includes at least one chemical group —S—H and/or —S—.

The dithio compounds described herein typically have a formula F—S—S—P, where "F" includes a fluorophore and "P" includes a non-fluorophore peptide. Other dithio compounds discussed herein have a formula D-S—S-A or D-S—S-Q, where "D" is a donor fluorophore, "Q" is a quencher, and "A" is an acceptor fluorophore. Related dithio compounds and methods for using dithio compound are described in U.S. application Ser. No. 11/512,485, filed on Aug. 30, 2006 and U.S. application Ser. No. 11/512,485, filed on Aug. 30, 2006, which are incorporated by reference herein in their entireties.

As used herein, a "fluorophore" is a chemical group that can be excited (e.g., by light or a chemical reaction) to emit fluorescence. Some suitable fluorophores may be excited by light to emit phosphorescence. As used herein, a "dye" may include a fluorophore. The dithio compounds described herein may include fluorophore selected from but not limited to: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD), 7-Hydroxy-4-methylcoumarin; 9-Amino-6-chloro-2-methoxyacridine; ABQ, Acid Fuchsin; ACMA (9-Amino-6-chloro-2-methoxyacridine); Acridine Orange; Acridine Red; Acridine Yellow; Acriflavin; Acriflavin Feulgen SITS A; Alexa Fluor 350™; Alexa Fluor 430™; Alexa Fluor 488™; Alexa Fluor 53:2™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminom ethyl coumarin (AMCA); Anil in Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAG 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hep; Coelenterazine ip; Coelenterazine n; Coelenterazine O; Coumarin Phalioidin; C-phycocyanine; CPM Methylcoumarin; CTC; CTC Formazan; Cy2™; Cy3.18; Cy3.5™; Cy3™; Cy5.1 8; Cy5.5™; Cy5™; Cy7™; Cyan GFP; cyclic AMP Fluorosensor (FiCRhR); Dabcyl; Dansyi; Dansyi Amine: Dansyl Cadaverine; Dansyl Chloride; Dansyl DHPE; Dansyi fluoride; DAPI; Dapoxyl; Dapoxyl 2; Dapoxyl 3; DCFDA; DCFH (Dichlorodihydrofluorescein Diacetate); DDAQ; DHR (Dihydrorhodamine 123); Di-4-ANEPPS; Di-8-ANEPPS (non-ratio); Di A (4-Di-16-ASP); Dichlorodihydrofluorescein Diacetate (DCFH); DiD—Lipophilic Tracer; DID (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysm; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilhamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBiazer (CCF2); GFP (S65T); GFP red shifted (rsGFP); GFP wild type, non-UV excitation (wtGFP); GFP wild type, UV excitation (wtGFP); GFPuv; Gloxailc Acid; Granular Blue; Haematoporphyrin; Hoechst 33258; Hoechst 33342; Hoechst 34580; HPTS; Hydroxy coumarin; Hydroxystilbamidine (FluoroGold); Hydroxy tryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 1488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 6.13]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; Spectrum Aqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21, SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-t; TO-PRO-3; TO-PRO-5; TOTO-1; TOTO-3; Tricolor (PE-Cy5); TRITC TetramethylRodamineIsoThioCyanate; True Blue; Trailed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore. Other suitable fluorophores may fluoresce after a chemical reaction in what is called luminescence, such as luciferin, which is a natural fluorophore becomes luminescent after the luciferase enzymatic reaction.

Fluorophores may include derivatives that have been modified to facilitate conjugation to another reactive molecule. As such, fluorophores may include amine-reactive derivatives such as isothiocyanate derivatives and/or succinimidyl ester derivatives of the fluorophore.

The dithio compounds may include a fluorophore selected from the group of xanthene-type fluorophores. The group of xanthene-type fluorophores typically includes any fluorophore that includes a xanthene group having the formula:

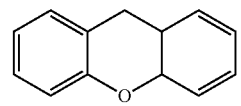 [SMILES: C1=CC2Cc3ccccc3OC2C=C1]

Xanthene-type fluorophores include fluorescein-type fluorophores (e.g., fluorescein and fluorescein isothiocyanate, and the like) and rhodamine-type fluorophores (e.g., rhodamine, rhodamine-B, and the like).

The dithio compounds may include a fluorophore selected from the group of fluorescein-type fluorophores. The group of fluorescein-type fluorophores typically includes any fluorophore that includes a fluorescein group having the formula:

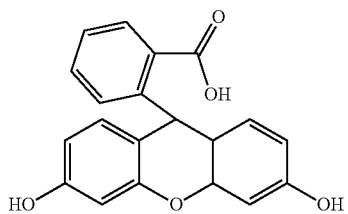 [SMILES: O=C(O)c1ccccc1C1c2ccc(O)cc2OC2C=C(O)C=CC21]

and derivatives and isomers thereof. Particularly useful derivatives include those with the carboxyl group replaced with any group that cannot cyclize (e.g., alkyl, haloalkyl, and halo groups). Other derivatives include those in which the carboxyl group is reacted with separate molecule (e.g., a nitrogen atom present in a separate molecule). For example, a derivative may be prepared by reacting fluorescein and piperazine where the carboxyl group of fluorescein reacts with the cyclic nitrogen atom of piperazine to form an amide linkage. The hydroxyl groups of the fluorescein molecule may be oxidized to ketones to form derivatives. The hydroxyl groups may be replaced with alkoxy groups to form derivatives (e.g., derivatives having methoxy or ethoxy groups in place of the hydroxyl groups).

Fluorescein-type fluorophores include fluorescein, fluorescein derivatives that include a fluorescein group, and salts thereof (e.g., 5-carboxy-2,7-dichlorofluorescein; 5-Carboxyfluorescein (5-FAM), DCFH (Dichlorodihydrofluorescein Diacetate); Fluorescein isothiocyanate (FITC); Fluorescein Diacetate, and the like).

The dithio compounds may include a fluorophore selected from the group of rhodamine-type fluorophores. The group of rhodamine-type fluorophores typically includes any fluorophore that includes a rhodamine group having the formula:

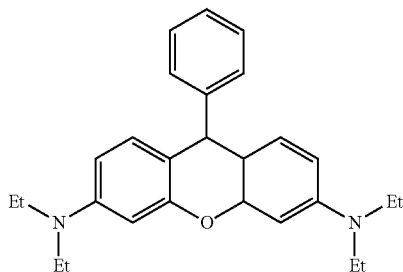 [SMILES: CCN(CC)C1=CC2Oc3cc(N(CC)CC)ccc3C(c3ccccc3)C2C=C1]

and isomers thereof.

Rhodamine-type fluorophores include rhodamine, rhodamine derivatives that include a rhodamine group, and salts thereof (e.g., 5-Carboxytetramethylrhodamine (5-TAMRA); 5-ROX (carboxy-X-rhodamine); 6-Carboxyrhodamine 6G; DHR (Dihydrorhodamine 123); Lissamine Rhodamine; Lissamine Rhodamine B; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Sulphorhodamine B can C; Sulphorhodamine G Extra; Tetramethylrhodamine (TRITC); X-Rhodamine; XRITC, and the like).

The dithio compounds may include a fluorophore selected from the group of the naphthalene-type fluorophores. The naphthalene-type fluorophores typically include any fluorophore that includes a naphthalene group having the formula:

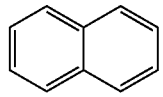

Naphthalene-type fluorophores include naphthalene, IAEDANS, EDAMS, and the like. Naphthalene-type fluorophores may include pyrene.

The fluorophore may include luciferin which is luminescent after reacting with ATP in a reaction catalyzed by luciferase. For example, the dithio compound may have a formula:

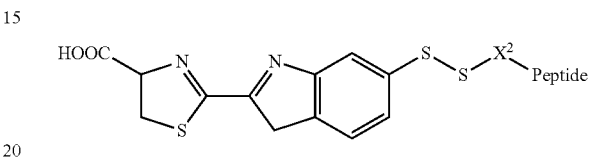

The dithio compounds described herein typically have a formula F—S—S—P, where "F" includes a fluorophore and "P" includes a non-fluorophore peptide. As used herein, a "non-fluorophore peptide" is a peptide that does not fluoresce when exposed to light (e.g., a peptide that does not fluoresce when exposed to visible light having a wavelength within a range of about 380-760 nm). In the compounds, the fluorophore typically exhibits dequenching when the dithio bond of the fluorophore is reduced. In the compounds, the fluorophore may be quenched via an interaction between the fluorophore and a quencher (or a quenching moiety) comprising at least one of the non-fluorophore peptide (P) and the dithio bond of the linker (S—S).

As used herein, the term "peptide" refers to a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

Suitable peptides for the dithio compounds contemplated herein may be primarily aliphatic in nature. For example, suitable peptides may include no aromatic amino acids or a low percentage of aromatic amino acids relative to total amino acids (e.g., where suitable peptides include no more than 20%, 10%, 5%, 3%, 1% aromatic amino acids, or alternatively include at least about 80%, 90%, 95%, 97%, 99% aliphatic amino acids). The term "aromatic amino acid" includes those amino acids having one or more aromatic moieties such as histidine (His or H), phenylalanine (Phe or F), tryptophan (Trp or W), and tyrosine (Tyr or Y). The term "aliphatic amino acid", includes, but is not limited to amino acids in the group consisting of alanine (Ala or A), cysteine (Cys or C), aspartic acid (Asp or D), glutamic acid (Glu or E), glycine (Gly or G), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), and valine (Val or V).

In the dithio compounds, the peptide is linked to the fluorophore via the disulfide linker. The peptide may be conjugated to the disulfide linker via an N-terminal amino group of the peptide, via a C-terminal carboxyl group of the peptide, or via a reactive group present in a side chain of one of the amino acids of the peptide. For example, the peptide may be conjugated to the disulfide linker via an amino group (e.g., of a lysine residue), a carboxyl group (e.g., of an aspartic acid residue or glutamic acid residue), or thiol group (e.g., of a cysteine residue) present in a side chain of one of the amino acids.

Typically, the amide linkages of the peptides are formed from an amino group of the backbone of one amino acid and a carboxyl group of the backbone of another amino acid. However, in some instances the amide linkages may be formed from an amino group of the backbone of one amino acid (e.g., cysteine) and a carboxyl group of a side chain of another amino acid (e.g. glutamate), such as in the glutathione tripeptide which may be present as a "non-fluorophore peptide" as contemplated in the fluorescent dithio compound contemplated herein. For example, the peptide of the dithio compound may comprise glutathione and the dithio compound may have a formula:

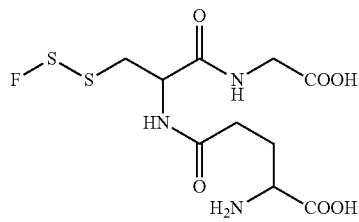 [SMILES: NC(CCC(=O)NC(CSSF)C(=O)NCC(=O)O)C(=O)O]

A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. The peptides of the dithio compounds disclosed herein typically are predominantly aliphatic and include few or no aromatic amino acids (less than about 20%. 10%, 5%, 3%, or 1% aromatic amino acids.) The polypeptides detected by the methods disclosed herein typically include one or more aromatic amino acids (and may include at least about 1%, 3%, 5%, or 10% aromatic amino acids).

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), Distinct from glycation, which is regarded as a nonenzymatic attachment of sugars, polysialylation (e.g., the addition of poly sialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The peptides present in the dithio compounds disclosed herein may exhibit one or more biological functions. In some embodiments, the peptide may exhibit biological transport or targeting activity (e.g., facilitating transport or retention of the dithio compound across a cell membrane or cell wall or into a cell organelle such as a nucleus, endoplasmic reticulum, mitochondria, or peroxisome). Peptides that exhibit biological transport or targeting activity include, but are not limited to, peptides comprising signal peptide sequences for eukaryotic or prokaryotic cells, the human immunodeficiency virus "Tat" peptide (e.g., the arginine-rich RNA-binding motif (ARM)), the arginine-glycine-aspartic acid or "RGD" peptides which target integrins and cancer cells, and the hormone ligands for cell surface receptors such as G-coupled protein cell surface receptors. (See, e.g. Said et al. Cell Mol Life Sci. (2010), 67(5):715-26. Epub 2009 Nov. 7; Schmidt et al., FEES Lett. (2010) May 3, 584(9):1806-13. Epub 2009 Nov. 16; Lai et al., Traffic. (2009) September, 10(9): 1243-56. Epub 2009 Jun. 15; Ozawa et al., AAPS J. 2010 May 6. [Epub ahead of print]; Colette et al, J Pept Sci. (2007) September, 13(9):568-74; Rashid et al., (2009); "Hmrbase: a database of hormones and their receptors," BMC Genomics 10(1): 307; Khar Heng Choo et al., "SPdb—a signal peptide database," BMC Bioinformatics 2005, 6:249; Cardarelli et al., Traffic (2008), 9:528-539 (describing the arginine-rich RNA-binding motif (ARM) of the Tat peptide); Erkki Ruoslahti, Annu. Rev. Cell Dev. Biol. (1996) 12:697-715; F. Sargent, Biochemical Society Transactions (2007), 35(5): 835-847; Cardarelli et al., Am. Soc. Gene Therapy (2007), 15(7): 1.313-1322; and Berks et al., Molec. Microbiology (2000) 35(2), 260-274; the contents of which are incorporated by reference herein in their entireties).

Peptides may be synthesized by any technique known to those of skill in the art, including the expression of peptides through standard molecular biological techniques, the isolation of proteins or peptides from natural sources, or the chemical synthesis of proteins or peptides. The nucleotide and peptide sequences corresponding to various genes have been previously disclosed, and may be found at computerized databases known to those of ordinary skill in the art. One such database is the National Center for Biotechnology Information's Genbank and GenPept databases. The coding regions for known genes may be amplified and/or expressed using the techniques disclosed herein or as would be know to those of ordinary skill in the art. Peptides also can be prepared using synthetic organic chemistry methods, such as solid phase synthesis where an amino acid's carboxylic acid is activated for amide bond formation with dicyclohexyl carbodiimide (Garrett & Grisham, Biochemistry, $2^{nd}$ edition, 1999, Brooks/Cole, 150). Alternatively, various commercial preparations of peptides and polypeptides are known to those of skill in the art.

The disclosed compounds include a fluorophore and a quencher, which may comprise at least one of the non-fluorophore peptide (P) and the dithio group (S—S) of the linker. In some embodiments, the fluorophore has an emission spectrum and the quencher has an absorption spectrum, such that the emission spectrum and absorption spectrum overlap. In particular, the emission spectrum and the absorption spectrum may overlap by about 20-100%, preferably about 40-100%, more preferably about 60-100%, and even more preferably about 70-100%. Overlap may be determined by determining the integral (i.e., area under the curve) for the absorbance versus wavelength for a given range of wavelengths (e.g., λ=450-750 nm) for any selected fluorophore and any selected quencher. Quenching may include dynamic quenching, static quenching, or both. Dynamic quenching may occur by FRET. Quenching may be relieved when the dithio group of the dithio compound is reduced, e.g., by reacting the dithio compound with a thiol-group that reduces the dithio compound. The quencher may be capable of altering the absorbance spectrum of the fluorophore. This alteration in absorbance may be relieved when the dithio group of the dithio compound is reduced, e.g., by reacting the dithio compound with a thiol-group that reduces the dithio compound. Quenching also may be relieved when the dithio compound undergoes a disulfide exchange reaction to form a more fluorescence mixed disulfide (e.g., by reacting the dithio compound with a disulfide on a protein), thereby forming new disulfide bonds between the probe and the protein.

The dithio compounds may include a fluorophore and a quencher that are present at a selected distance within the compounds, e.g., at a distance of about 6-100 angstroms, preferably 15-75 angstroms, more preferably about 30-70 angstroms. In some embodiments, the fluorophore and the quencher are present at a distance of about 3-100 angstroms, preferably 3-75 angstroms, more preferably about 3-50 angstroms. The fluorophore and the quencher may be present in the dithio compounds at a distance that is suitable to permit FRET. In some embodiments, the fluorophore and the quencher are present in the compound at a distance of no more than about 20 angstroms. The fluorophore and the quencher may be present in the dithio compounds at a distance that is suitable for static quenching. In some embodiments, the quencher is the disulfide itself, which is only able to quench if the peptide is predominantly comprised of aliphatic amino acids (e.g., where the peptide comprises at least about 80%, 90%, 95%, 97%, or 99% aliphatic amino acids, or includes no aromatic amino acids and is 100% aliphatic amino acids).

The distance between the fluorophore and the quencher may be designed by selecting a dithio linker that has a selected length. As used herein, a dithio linker may have a formula —$X^1$—S—S—$X^3$—, the $X^1$ group and the $X^2$ group may be the same or different and selected from $C_{1-18}$ alkyl groups, alkenyl groups, alkynyl groups, aryl groups and combinations thereof, optionally substituted with at least one reactive group (e.g., —$NH_2$ or —COOH). The length of the dithio linker may be designed by selecting a suitable $X^1$ group and a suitable $X^2$ group, e.g., an $X^1$ group and an $X^2$ group that have a suitable number of carbon atoms to provide a selected length for the dithio linker. Suitable linkers include cystamine or cystamine derivatives, such as compounds having the formula;

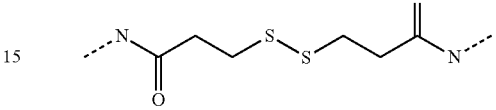

The dithio compound may have a formula F—$X^1$—S—S—$X^2$—P, in which "F" includes a fluorophore and "P" includes a peptide, and at least one of the $X^1$ group and the $X^2$ group include a chemical group that is capable of influencing at least one of the emission spectrum and absorbance spectrum of the fluorophore. At least one of the $X^1$ group and the $X^2$ group may include a chemical group that is capable of influencing the emission spectrum of the fluorophore. At least one of the $X^1$ group and the $X^2$ group may include an aryl group or an allyl group. In some embodiments, the aryl group may be selected from a phenyl group and a pyridinyl group, which may be optionally substituted with at least one of alkyl groups, haloalkyl groups, halogen groups, alkyl ester groups, ether groups, carboxyl groups, amide groups, and nitro groups.

For example, at least one of $X^1$ and $X^2$ may include an aryl group. The aryl group may be substituted with an amide group. In some embodiments at least one of $X^1$ and $X^2$ includes a group having a formula selected from:

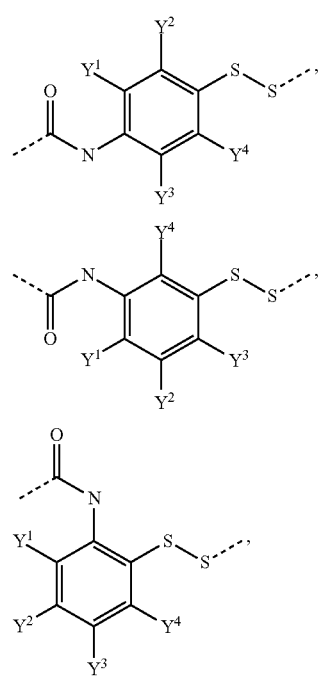

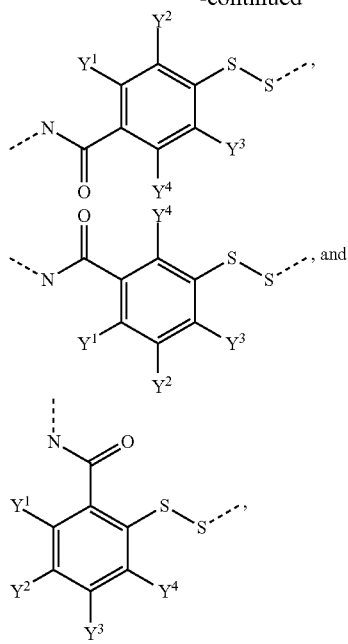

wherein $Y^1$, $Y^2$, $Y^3$, and $Y^4$ may be the same or different and are hydrogen or halide (i.e., H, F, Cl, Br, or I).

In one suitable embodiment, at least one of $X^1$ and $X^2$ includes a group having a formula:

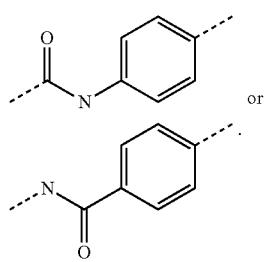

or

The dithio compound may include derivatives of cystamine or diaminodiphenyldisulfide (herein referred to as "DAPS"). In some embodiments, the dithio compound may include derivatives of p,p'-diaminodiphenyldisulfide, m,m'-diaminodiphenyldisulfide, and o,o'-diaminodiphenyldisulfide.

In suitable embodiments, the dithio compound has the formula:

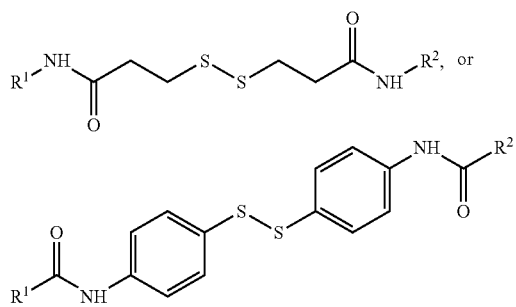

in which $R^1$ includes a fluorophore group and $R^2$ includes a non-fluorophore peptide group.

The dithio compound may have a formula "FITC-DAPS-P" or "P-DAPS-FITC", which are used interchangeably herein to refer to a dithio compound that includes a fluorescein-type fluorophore and a non-fluorophore peptide linked by a diaminodiphenyldisulfide linker, (which may include p,p'-diaminodiphenyldisulfide linkers, m,m'-diaminodiphenylsulfide linkers, and o-o'-diaminodiphenyldisulfide linkers). "F-CYST-P" and "P-CYST-F" are used interchangeably herein to refer to a dithio compound that includes a fluorescein-type fluorophore and a non-fluorophore peptide linked by a cystamine linker.

In some embodiments, the dithio compounds may include a fluorescein-type fluorophore as a fluorophore and a non-fluorophore peptide, which are present in the dithio compounds at a distance of about 10-60 angstroms (e.g., 40-60 angstroms). The dithio compounds may include a naphthalene-type fluorophore as a fluorophore and a non-fluorophore peptide, which are present in the dithio compounds at a distance of about 10-60 angstroms (e.g., 40-60 angstroms). The dithio compounds may include a DANSYL-type fluorophore as a fluorophore and a non-fluorophore peptide, which are present in the dithio compounds at a distance of about 10-50 angstroms (e.g., 25-45 angstroms).

The dithio compounds may be prepared by any suitable method. For example, the dithio compounds may be prepared by reacting precursors that include: (A) a first precursor that includes a fluorophore, (B) a second precursor that includes a peptide; and (C) a dithio reagent (i.e., a dithio linking reagent) having the formula $X^1$—S—S—$X^2$, where $X^1$ and $X^2$ may be the same or different and each includes at least one reactive group capable of reacting with the first precursor and the second precursor. The fluorophore and the peptide may include reactive groups as described herein. The dithio compounds that include a fluorophore and a peptide (and which may be prepared by the methods described herein) may have a formula F—$X^3$—S—S—$X^4$—P where "F" Includes a fluorophore and "P" includes a peptide $X^3$ and $X^4$ may be the same or different and may include aryl groups.

For example, the dithio compounds may be prepared by reacting a reaction mixture that includes: (a) a dithio linking agent with two or more first reactive groups; (b) a fluorophore having at least one second reactive group; and (c) a peptide having a third reactive group. The second and third reactive groups may be the same or different. In some embodiments, the fluorophore (or peptide) may be reacted with the dithio linker to form an intermediate reaction product that is at least partially purified and subsequently reacted with the peptide (or fluorophore, respectively). Suitable reactive groups may include nucleophilic groups and electrophilic groups, (e.g., nucleophilic groups and electrophilic groups capable of reacting with each other). Reactive groups may include amino groups and amine-reactive groups (e.g., isothiocyanate groups, succinimidyl ester groups, carboxyl groups, sulfonyl groups, and the like). Suitable dithio linking agents for preparing the dithio compounds may include cystamine and diaminodiphenyl disulfide.

Amine-reactive fluorophores may be derivatized by reacting with groups such as isothiocyanates (yielding thioureas) or succinimidyl esters (yielding carboxamides). Reactions then may be performed with dithio linking reagents that include a reactive amine (e.g., —$NH_2$) and a dithio group. For example, the dithio linking reagent, may a formula $NH_2$—$X^1$—S—S—$X^2$—$NH_2$, in which $X^1$ and $X^2$ may be the same or different and may include $C_{1-18}$ (preferable $C_{1-18}$) alkyl, alkenyl, alkynyl, or aryl, which may be optionally substituted with at least one heteroatom selected from N, P, and O. To separate reaction products (e.g., F—S—S—F, F—S—S-Q and Q-S—S-Q, where F=fluorophore and Q=quencher) HPLC may be performed. Useful reagents for synthesizing dithio compounds as contemplated herein may include, but are not limited to, cysteine, β-mercaptoethanamine, cystamine, diamine diphenyl disulfide, and mixtures thereof.

Suitable peptides for synthesizing the dithio compounds contemplated herein may include a cysteine residue. In some embodiments, a cysteine residue is added to the peptide at the N-terminus or C-terminus of the peptide. For example, the dithio compounds contemplated herein may have a formula:

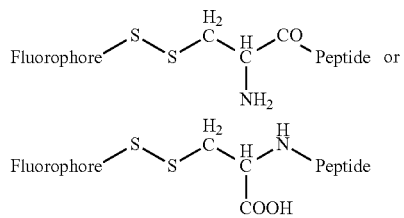

When a peptide contains a thiol, such as would be the case when the peptide contains a cysteine or homocysteine amino acid, it may be desirable to form a disulfide of that peptide by oxidizing the thiol to a disulfide:

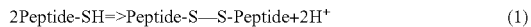

(1)

This reaction is well known in the art, and can be facilitated in a number of ways, including treatment in basic conditions, or exposure to a mild oxidizing agent. For example, one can treat with iodine ($I_2$) or simply air-oxidize (so $O_2$ is the oxidant). This reaction is described in introductory organic chemistry textbooks, such as Organic Chemistry 5e, Brown, Foote, Iverson & Anslyn, Brooks/Cole, 2011, p. 413. One can also oxidize the thiol to a disulfide using potassium ferricyanide, as described by Hope, Murti and Vigneaud (1962) J. Biol. Chem. 237, p. 1564. Another method, using silyl chloride-sulfoxide, was described by Akaji et al (J. Am. Chem. Soc (1992) 114, 4137-4143). A method to form disulfides on-resin, as part of a solid phase synthesis, was described by Galande et al. ((2005) J. Comb. Chem. 7, 174-177). A particularly simple and effective way of forming disulfides was reported by Tam et al ((1991) J. Am. Chem. Soc. 113, 6657-6662) using DMSO as oxidant, such as by incubating in a 20% aqueous solution.

After the disulfide is formed, one can perform a disulfide exchange reaction with a fluorophore tethered via a disulfide bind, such as F-linker-S—S-linker-F where F is a fluorophore, such as fluorescein, or one of the Alexa or Cy dyes, and "linker" could refer to the aromatic linker, such as that in our present probe using the para-substituted benzene (4-thioaniline), or the cystamine linker. This disulfide exchange reaction would proceed as follows:

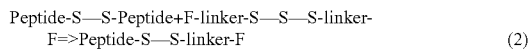

Figure 2:
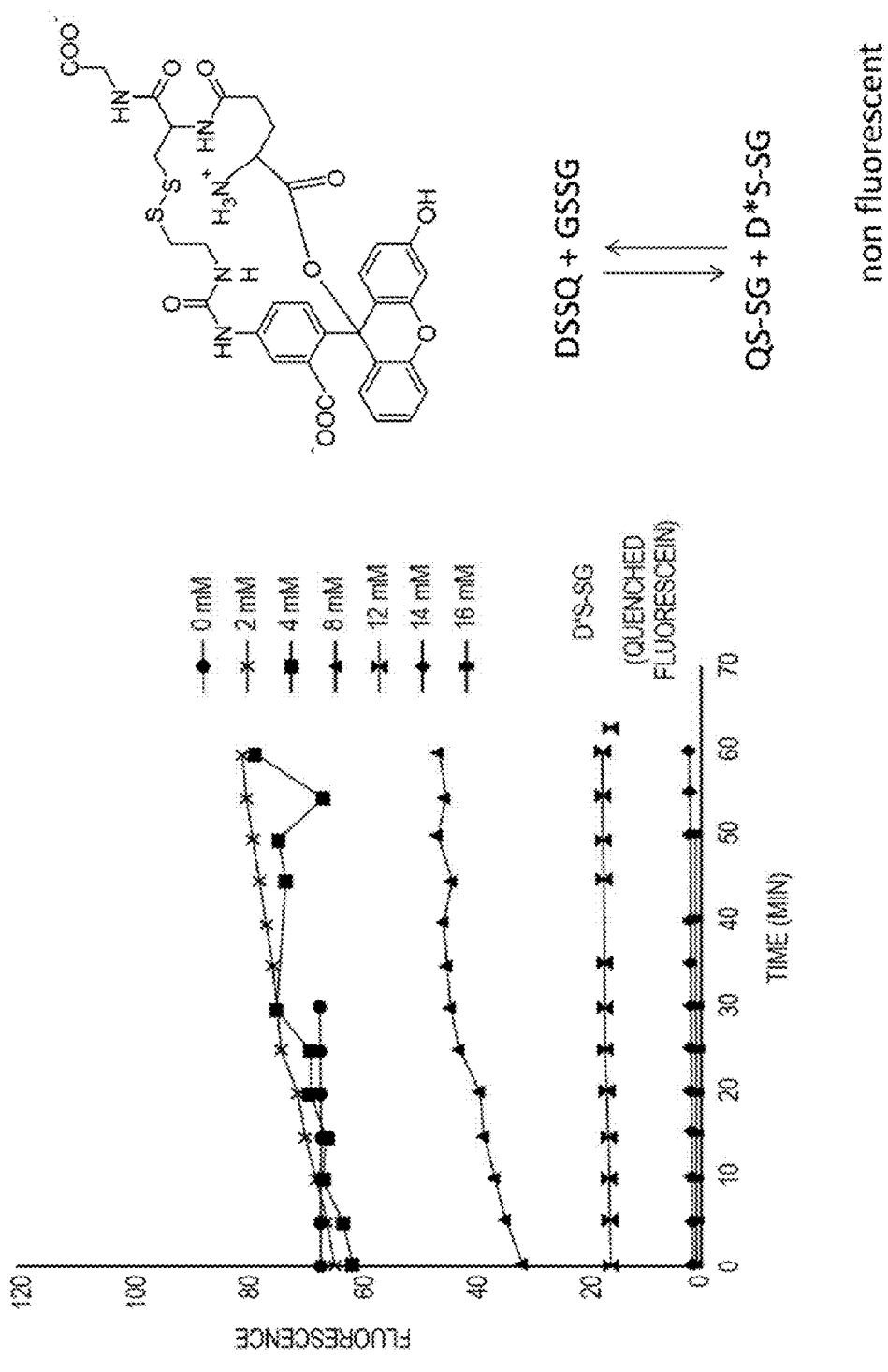
FIG. 2. illustrates that the F—$X^1$S—S-glutathione mixed disulfide can be trapped by reacting the fluorescent dithio probe with G-S—S-G in the disulfide exchange reaction.

(2)

as a mixture of products. The desired Peptide-S—S-linker-F mixed disulfide could then be purified, by methods such as HPLC, using a reversed phase resin (ex. a CIS column), or by silica gel chromatography. The peptide used could be any peptide desired, as long as it contains one cysteine amino acid, preferable at the amino or carboxy terminus. In some embodiments, the fluorophore is quenched most, effectively when an aliphatic peptide of length ≤20 and preferably ≤12 amino acids is used. For example, if the peptide is the glutathione tripeptide, the fluorophore is completely quenched (FIG. 2). Methods for peptide synthesis, including solid phase synthesis, are well known in the art, companies provide peptides as contract services, and there are even automated peptide synthesis machines to provide peptides of any desired sequence. Especially desirable peptides for the disclosed methods are those that signal for transport to cellular organelles, such as the nucleus, mitochondria, peroxisomes, the golgi apparatus, and the endoplasmic reticulum. Other useful peptides are those that target molecules to cancer cells, such as the RGD peptides. Still other useful peptides are those that facilitate transport across cell walls or membranes, such as the Tat peptides. Still other useful peptides are hormones that frequently target and bind to cell surface receptors, such as GPCR proteins. Such peptides include, but are not limited to, growth, hormone. Insulin, various growth factors (ex. VEGF, TGF) and hormones, as well as neuroactive peptides.

In some embodiments of the invention, one would use purified peptide, such as that prepared in reaction (2), in cell biology studies (ex. imaging cells using confocal microscopy). In other embodiments, one might provide the F-linker-S—S-linker-F as part of a kit, with a procedure for the user to react their Peptide-SH (or Peptide-S—S-Peptide) of interest, in situ, to produce their own Peptide-S—S-linker-F for cellular studies, such as confocal imaging of thiols or disulfides in cells.

Also disclosed herein are methods for detecting thiol-containing and/or dithio-containing compounds. In some embodiments the methods include (A) reacting a reaction mixture to form at least one reaction product; and (B) detecting the at least one reaction product. Typically, the reaction mixture will include (i) the thiol-containing compound and/or the dithio-containing compound; and (ii) a fluorescent dithio compound as described herein. The reaction mixture may be formed in vitro, in vivo, or in situ. The reaction mixture may be present in a cell. The fluorescent dithio compounds may be used to detect thiol-containing compounds and/or dithio-containing compounds in biopsy methods. The fluorescent dithio compounds may be used to detect thiol-containing compounds and/or dithio-containing compounds by monitoring tissue sample fluorescence levels quantitatively in a fluorimeter or with a fluorescence microscope, or qualitatively by using the disclosed fluorescent dithio compounds as a component of a histological stain. Methods for using the fluorescent dithio compounds disclosed herein for detecting thiol-containing compounds and/or dithio-containing compounds are described in U.S. application Ser. No. 11/512,485, filed on Aug. 30, 2006 and U.S. application Ser. No. 11/512,485, filed on Aug. 30, 2006, which are incorporated by reference herein in their entireties.

Suitable dithio compounds for the methods for detecting thiol-containing compounds include dithio compounds having a formula F—S—S—P, in which, "F" includes a fluorophore and "P" includes a non-fluorophore peptide. In the methods for detecting thiol-containing compounds and dithio-containing compounds as described herein, detecting the at least one reaction product may include observing dequenching of the fluorophore or altered fluorescence of the fluorophore. Dequenching or altered fluorescence may occur when the dithio compounds react with thiols that reduce the disulfide bond to form the F—S—H fluorophore (as in FIG. 1), or when the dithio compounds react with another dithio in a disulfide exchange reaction to form a new mixed disulfide.

The methods may be used to detect any suitable thiol-containing compound and/or dithio-containing compound. Suitable compounds include any thiol- and/or dithio-containing compound that is capable of reducing the fluorescent dithio compound at the dithio bond of the fluorescent dithio compound. For example, the methods may be used to detect thiol-containing compounds such as glutathione, homocysteine, cysteine-containing peptides or proteins, ADPβS, GDPβS, and combinations thereof. Suitable dithio-containing compounds include any dithio-containing compound that is capable of reacting with the fluorescent dithio compound at the dithio bond of the fluorescent dithio compound. Such dithios could include those in oxidized membrane-bound or membrane-associated proteins such as the *E. coli* Dsb system, and its eukaryotic homologs, as well as lipid transport proteins like apoE and lipovitellin, cytokines, and C-reactive proteins (CRP). The methods for detecting thiol-containing compounds and/or dithio-containing compounds may be performed in vitro, in vivo, and/or in situ. The methods may be performed in cells. For example, the methods may be performed by administering the fluorescent dithio compounds to tissue or cells in which the compounds react with at least one thiol-containing compound and/or dithio-containing compound to form at least one reaction product.

The methods may include detecting the at least one reaction product, e.g., by fluoroscopic methods known in the art. Detecting the at least one reaction product may include detecting dequenched fluorescence of the fluorophore in a reaction product using fluoroscopic methods known in the art. Defecting the at least one reaction product may include detecting an increase or decrease in absorbance by the fluorophore using fluoroscopic methods known in the art. Detecting the reaction product in a reaction of the dithio compounds with thiols, will involve detecting F—S—H, and its salts Detecting the reaction product in a reaction of the dithio compounds with dithios, will involve detecting F—S—S-polypeptide where the polypeptide was a dithio protein that reacted with the original F—S—S-peptide probe. Typically, aliphatic peptides lead to the fluorophore being quenched in the dithio compounds contemplated herein, but polypeptides do not quench. Therefore, the dithio exchange reaction permits detection of polypeptide disulfides (i.e., F—S—S-polypeptide).

The methods for detecting thiol-containing compounds and/or dithio-containing compounds as described herein may be performed continuously or in real-time. As used herein, "real-time" methods are methods in which the thiol-containing compound is defected contemporaneously as it is formed in a reaction mixture (e.g., as it is formed in vitro or in cells).

ILLUSTRATIVE EMBODIMENTS

The following embodiments are illustrative and not intended to limit the claimed subject matter.

Embodiment 1

A dithio compound having a formula F—S—S—P wherein F comprises a quenched fluorophore and P comprises a peptide.

Embodiment 2

The dithio compound of embodiment 1 having a formula:

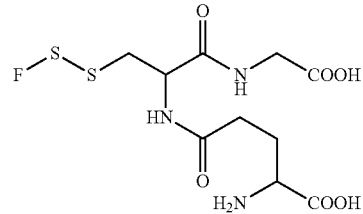

Embodiment 3

The dithio compound of embodiment 1 having a formula:

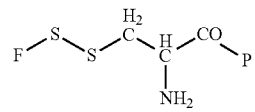

Embodiment 4

The dithio compound of embodiment 1 having a formula:

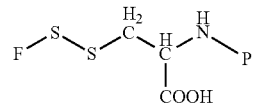

Embodiment 5

The dithio compound of any of embodiments 1-4, wherein the peptide comprises a signal peptide sequence.

Embodiment 6

The dithio compound of any of embodiments 1-5, wherein the peptide comprises the arginine-rich RNA-binding motif (ARM) of the human immunodeficiency virus Tat peptide.

Embodiment 7

The dithio compound of any of embodiments 1-6, wherein the peptide comprises an RGD sequence.

Embodiment 8

The dithio compound of any of embodiments 1-7, wherein the peptide comprises a hormone ligand for a G-coupled cell surface receptor.

Embodiment 9

The dithio compound of any of embodiments 1-8, wherein the peptide comprises an amino acid targeting sequence for a cellular nucleus.

Embodiment 10

The dithio compound of any of embodiments 1-9, wherein the peptide comprises an amino acid targeting sequence for a cellular endoplasmic reticulum.

Embodiment 11

The dithio compound of any of embodiments 1-10, wherein the peptide comprises an amino acid targeting sequence for a cellular mitochondria.

Embodiment 12

The dithio compound of any of embodiments 1-11 having a formula:

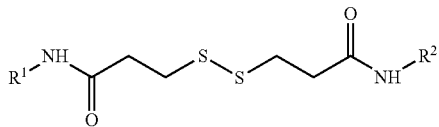

wherein $R^1$ comprises a fluorophore and $R^2$ comprises a peptide.

Embodiment 13

The dithio compound of any of embodiments 1-12, wherein the peptide comprises no more than 20 amino acids and comprises no aromatic amino acids.

Embodiment 14

The dithio compound of any of embodiments 1-12, wherein the peptide comprises no more than 12 amino acids and comprises no aromatic amino acids.

Embodiment 15

A method for preparing a dithio compound having a formula F—S—S—P wherein F comprises a quenched fluorophore and P comprises a peptide, the method comprising reacting precursors that include: (A) a first precursor that comprises a fluorophore; (B) a second precursor that comprises a peptide; and (C) a dithio reagent having a formula $X^1$—S—S—$X^2$, wherein $X^1$ and $X^2$ may be the same or different and each comprise reactive groups capable of reacting with the first precursor and the second precursor.

Embodiment 16

The method of embodiment 15, further comprising adding one or more cysteine residues to the N-terminus or C-terminus of the peptide in order to prepare the second precursor.

Embodiment 17

A method for detecting a thiol- or dithio-containing compound, the method comprising: (A) reacting a dithio compound having a formula F—S—S—P wherein F comprises a quenched fluorophore and P comprises a peptide with the thiol- or dithio-containing compound to form at least one reaction product; and (B) defecting the at least one reaction product.

Embodiment 18

The method of embodiment 17, wherein the thiol- or dithio-containing compound is a protein.

Embodiment 19

A method of preparing a dithio compound having a formula F—S—S—P wherein F comprises a quenched fluorophore and P comprises a peptide, the method comprising reacting precursors that include: (A) a first precursor having a formula F—S—S—F, and (B) a second precursor having a formula P—S—S—P.

Embodiment 20

A kit comprising: (a) a reagent having a formula F—S—S—F; and (b) a reagent having a formula P—S—S—P; wherein F is a fluorophore and P is an aliphatic peptide.

EXAMPLES

The following examples are illustrative and not intended to limit the claimed subject matter.

Reaction of Dithio Probe with GSH Gives a Rapid Decrease in Fluorescence First Before Increasing.

Referring to FIG. 1, shown is a thiol reaction with the fluorescent probe DSSA (sometimes also called DSSQ) where D is fluorescein and A is para-methyl red, a fluorescein quencher. The thiol reactant in this case is the glutathione tripeptide (GSH) at 2 mM, 4 mM, 8 mM and 15 mM. DSSA probe is present at a much lower concentration, of 50 uM. Reduction of any dithio probe, such as this probe (as well as a F—$X^1$—SS—$X^2$-peptide), by a thiol such as the glutathione tripeptide, goes through a two-step process. The thiol is in excess relative to DSSA, so eventually a free fluorophore (DS) is obtained, which is more fluorescent than DSSA. The fluorescence emission spectra are shown in FIG. 1, for reaction over time at different concentrations of glutathione. Notably, there is an initial decrease in fluorescence (due to rapid formation of the DS—SG intermediate shown), followed by an increase (due to subsequent formation of DS). Notably, the DSSA probe shown here still has significant fluorescence signal before reaction with glutathione, and it goes through a two-step reaction (making reading of fluorescence intensity more complicated). It is desirable that a probe have a lower background fluorescence and not show the complication of a two-step reaction process in the fluorescence spectra.

Mixed Disulfide Intermediate can be Trapped by Reacting with GSSG

Figure 3:
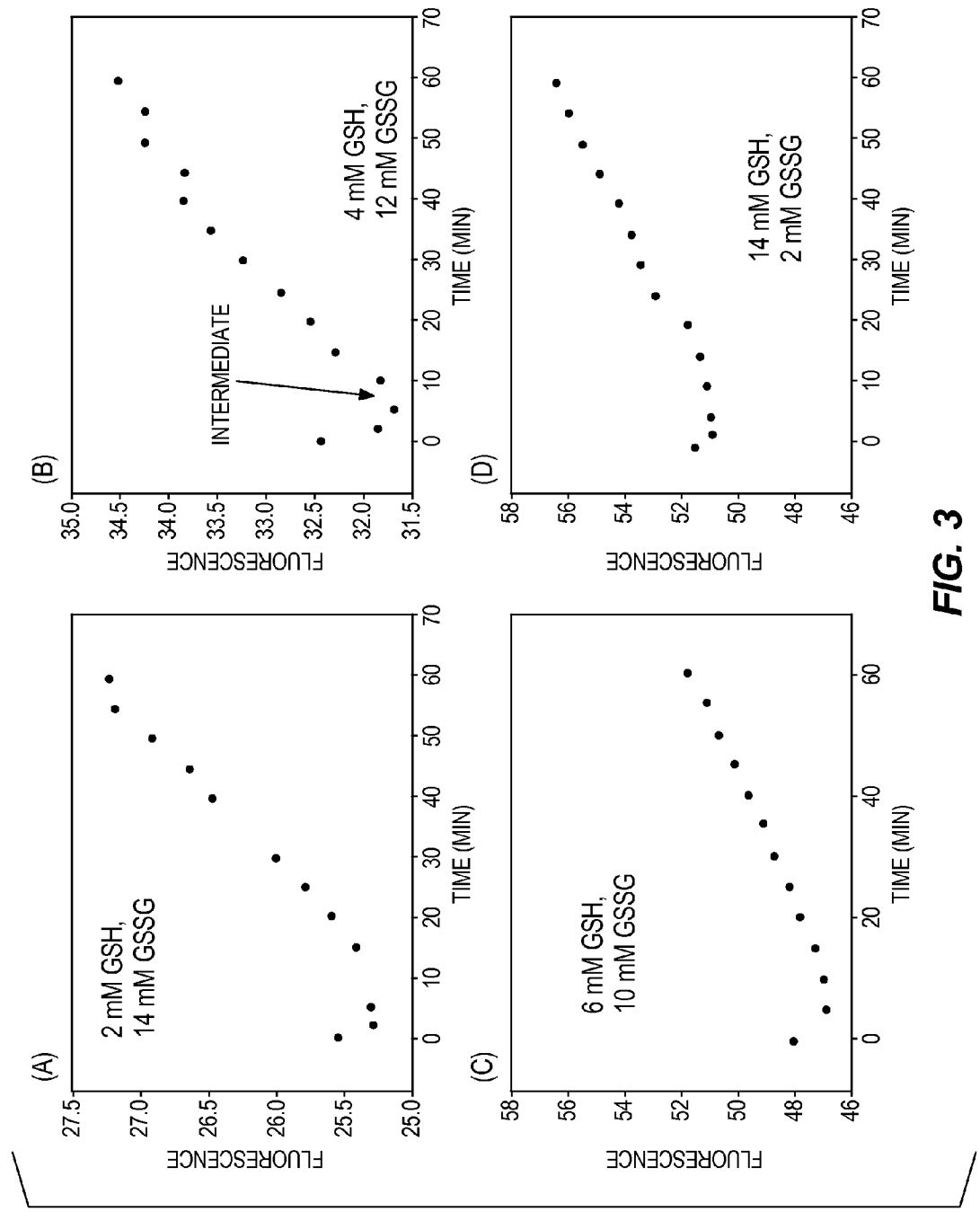
FIG. 3. illustrates that in the presence of increasing G-S—S-G an increase in the level of the F—$X^1$—S—S-glutathione mixed disulfide is observed.
Figure 4:
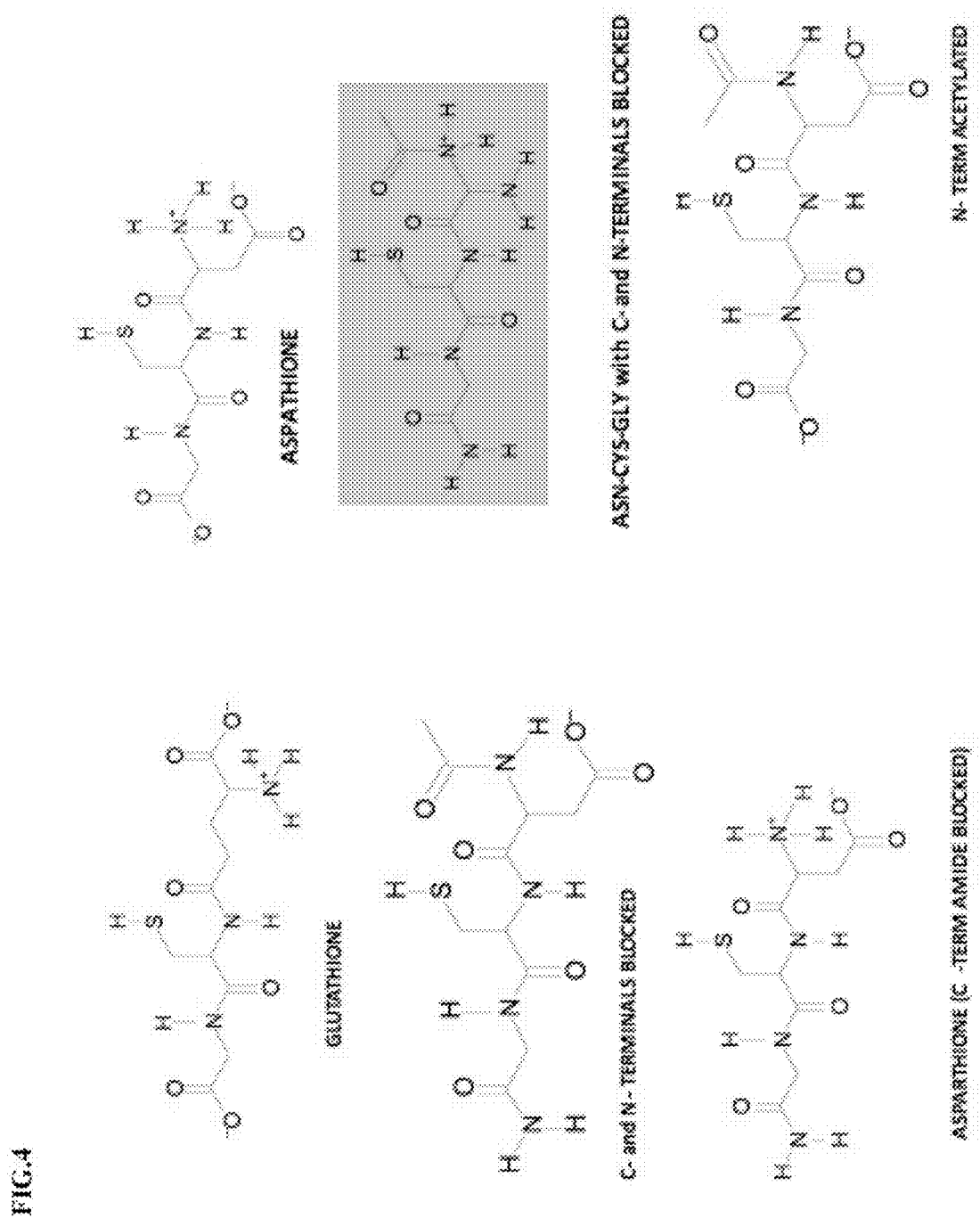
FIG. 4. illustrates analogs of glutathione (G-S—H) with nucleophilic positions blocked.

Referring to FIG. 2, shown is the fluorescence intensity after reaction of the probe from the previous example, but this tune in a reaction with the glutathione peptide disulfide, GSSG (rather man the reduced form of glutathione, FIG. 1). In this case, one would expect only a disulfide exchange reaction according to the following reaction sequence: DSSQ+GSSG=>DSSG+QSSG, where D is fluorescein and GSH is glutathione. The product of this disulfide exchange reaction is the same as the intermediate that was produced in FIG. 1. However, FIG. 2 demonstrates that the DSSG intermediate, where fluorescein is tethered to the glutathione tripeptide via a disulfide bond, is even more quenched than fluorescein in the context of the original DSSQ probe. In FIG. 3, it can be seen that by making mixtures of reduced glutathione (GSH), with relatively higher concentrations of the oxidized disulfide form (GSSG), there is increased level of the highly quenched intermediate (FIG. 3). This again confirms that the DSSG intermediate is highly quenched, but can undergo further reduction (in the presence of excess GSH thiol) to form DS. This is in contrast to a pure disulfide exchange reaction, as shown in FIG. 2, where DSSG is the final product. This DSSG intermediate is one form of the F—$X^1$—SS—$X^2$—P dithio compound as disclosed herein where P is a peptide. This remarkable decrease in fluorescence that was observed upon forming the mixed disulfide with the glutathione tripeptide was unexpected. These data demonstrate that the F—$X^1$—SS—$X^2$—P dithio compound is nonfluorescent and would make a better reagent for imaging thiols and disulfides than the reagent in FIG. 1. In order to test whether some reactive nucleophilic atom on glutathione attacked the fluorescein ring, leading to loss of fluorescence, as shown in the structure in FIG. 2, glutathione analogs were created having different nucleophilic position chemically blocked (shown in FIG. 4). It was found that all of these glutathione analogs reacted with the original DSSA probe in the same manner, with an initial decrease in fluorescence due to formation of the F—$X^1$—SS—$X^2$—P intermediate (where P is the modified glutathione peptide). Accordingly, quenching is occurring not because of a nucleophilic or reactive atom on the peptide (as suggested by the proposed structure in FIG. 2), but rather because the peptide is aliphatic in nature. Subsequent studies, including quantum mechanical calculations, have shown that the disulfide is able to quench the fluorophore if an aliphatic peptide is present, but not if aromatic residues or chemical groups (as in para-methyl red in FIG. 1) are present. Accordingly, a preferred reagent for detecting thiols and disulfides is a fluorophore tethered, via a disulfide bond, to a peptide, because it has a lower fluorescent background signal and less complicated reaction kinetics (i.e., a one step reaction).

Synthesis of Dithio Probes.

Figure 5:
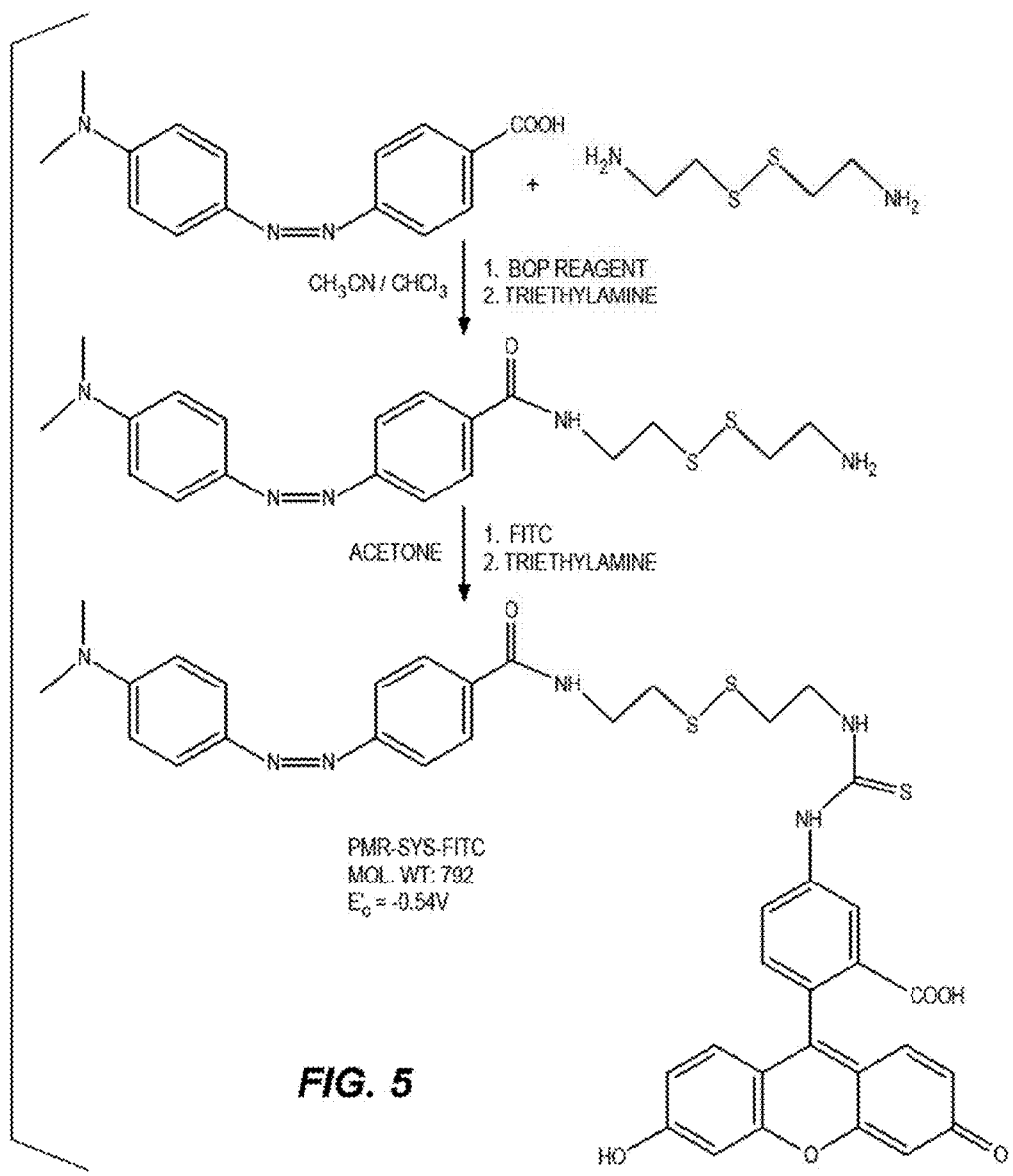
FIG. 5. illustrates the synthesis of a dithio probe comprising para-methyl red, cystamine disulfide, and fluorescein.

The DSSA probe that was used in FIG. 1 was synthesized as shown in FIG. 5. Synthesis of a DSSD probe, where two identical fluorophores are tethered via a disulfide bond, could be accomplished using a slight modification of the procedure shown in FIG. 5. Briefly, the first, reaction to link para-methyl red and the cystamine disulfide is omitted and excess fluorescein isothiocyanate is reacted directly with the cystamine disulfide.

Detection of Proteins, and Fluorescent Properties of DSS-(Protein).

Figure 6:
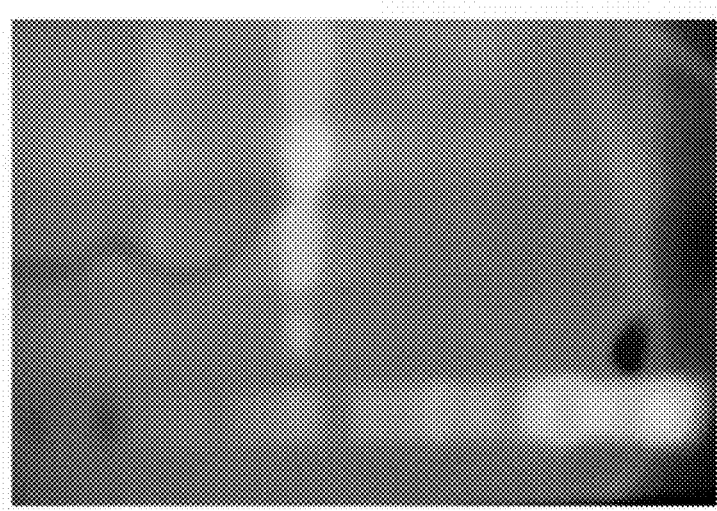
FIG. 6. illustrates a fluorescent image of an SDS PAGE gel of rabbit muscle glyceraldehyde-3-phosphate dehydrogenase, after labeling protein to produce FSS-protein.
Figure 7:
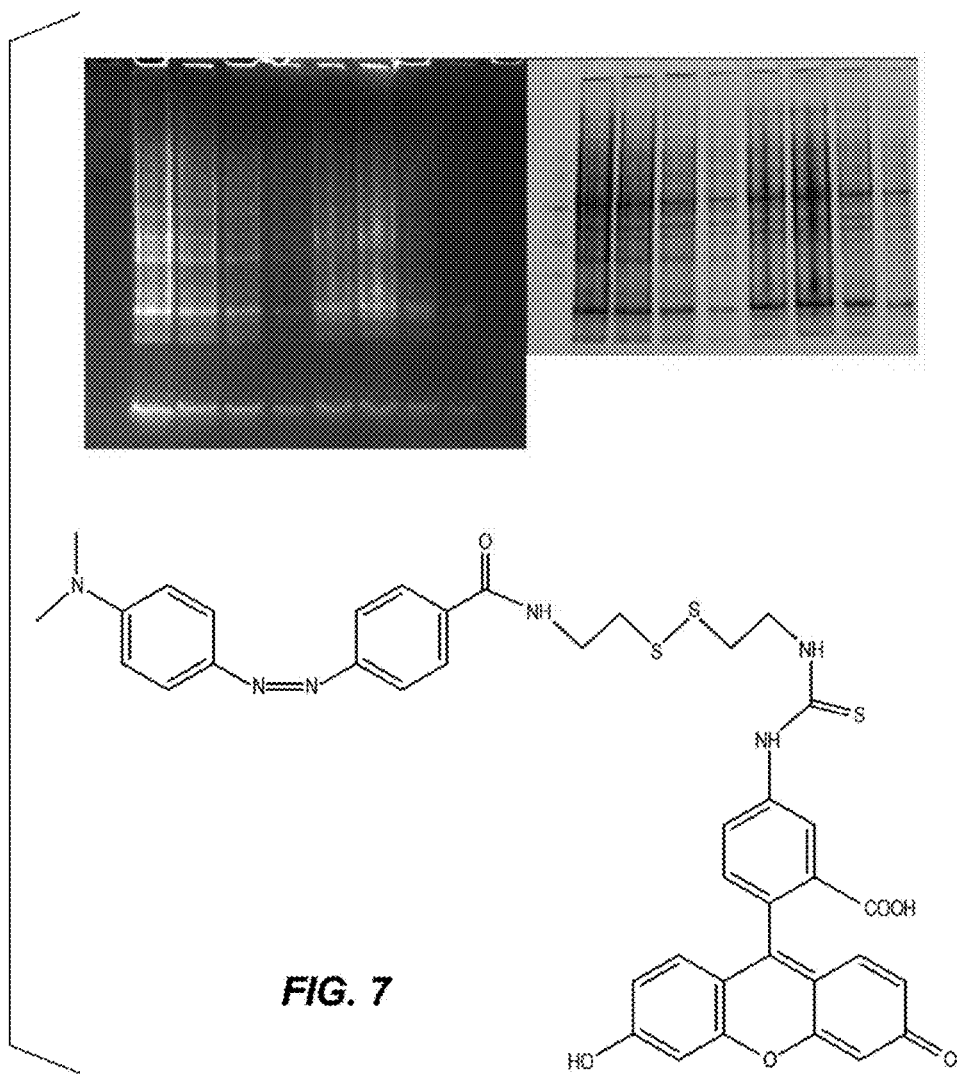
FIG. 7. illustrates a fluorescent image of an SDS PAGE gel of proteins from bovine lung cells, after labeling protein to produce FSS-protein (left panel). Right panel is the analogous gel, but stained using coomassie.

While previous data have demonstrated that the F—$X^1$—SS—$X^2$-Peptide is not fluorescent (see FIG. 2), if proteins (more generally, polypeptides) are reacted with dithio probes, for example by reacting proteins in an SDS PAGE gel with DSSQ, they are in fact fluorescent. Therefore, F—$X^1$—SS—$X^2$-Polypeptide is fluorescent, even though F—$X^3$—SS—$X^2$-Peptide is not fluorescent. For example, reaction of rabbit muscle glyceraldehyde-3-phosphate dehydrogenase in an SDS PAGE gel led to a strong fluorescent signal (FIG. 6), and reaction of the proteins extracted from bovine lung cells, also led to fluorescent signals (FIG. 7). The fact that F—$X_1$—SS—$X^2$-Peptide is not fluorescent (FIG. 2), and yet can be converted to F—$X^1$—SS—$X^2$-Protein via a simple disulfide exchange reaction, suggests that the F—$X^1$—SS—$X^2$-Peptide dithio compound is a suitable reagent for detecting dithio groups on proteins (but not on peptides like GSSG; see FIG. 2). This is an unexpected and highly useful property of fluorescent dithio reagents such as F—$X^1$—SS—$X^2$-Peptide, where these reagents can be utilized in methods for detecting dithio groups on proteins.

Confocal Microscopy Imaging.

Figure 8:
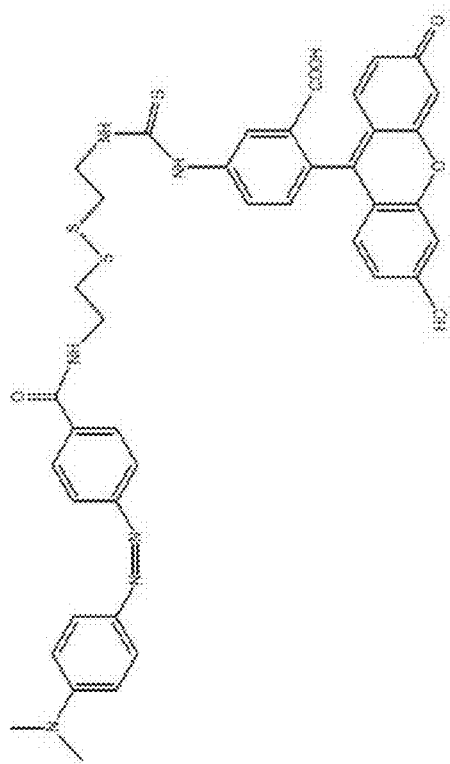
FIG. 8. illustrates images of a zebrafish embryo, using a Nikon confocal microscope, showing bright field image (A) and corresponding fluorescence image (B) after excitation at 490 nm. Fish was exposed to the dithio probe shown in order to label thiol and disulfide proteins. Panel B shows that only proteins in the chorion (identified with the arrow) were labeled.
Figure 8:
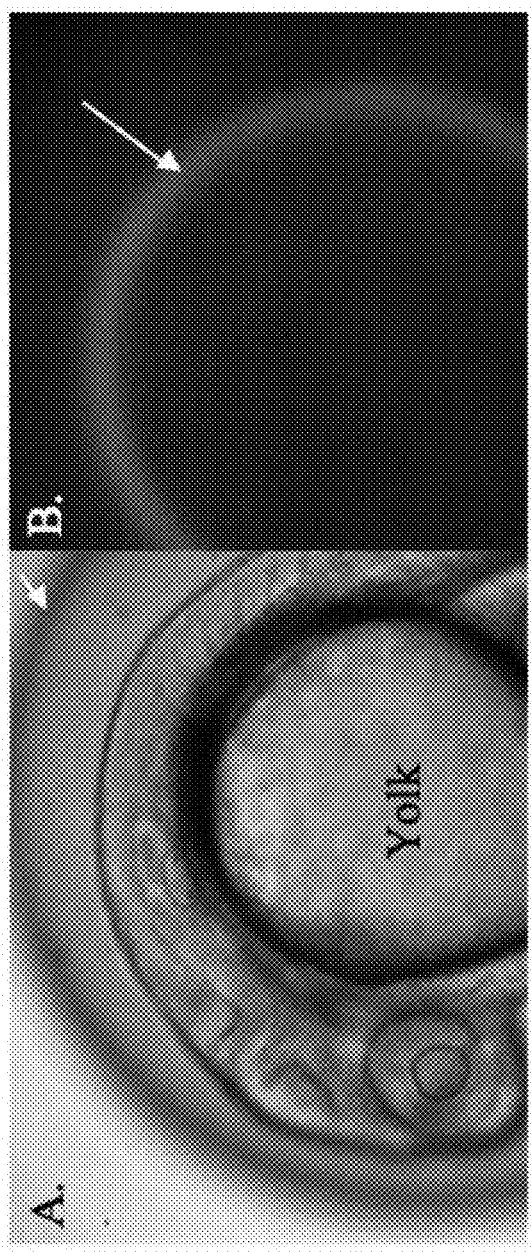

Fluorescent dithio probes can be used to label proteins in live cells. If the DSS-(protein) formed is fluorescent, then it can be visualized using confocal microscopy. This is shown in FIG. 8, where the chorion of zebrafish embryos was labeled using a fluorescent dithio probe. The bright field image (FIG. 8A) shows the fish wrapped around the yolk, and the outer layer (identified with an arrow) is the protective chorion layer. The fluorescence image in panel B is the result of excitation at 490 nm, and shows that fluorescence signal is coming from proteins in the chorion. Interestingly, fluorescence signal was also obtained, even if thiols were first blocked using iodoacetamide. This suggests that labeling was of dithio containing proteins (i.e. oxidized thiols). If so, this represents the first report of imaging of dithio groups inside live cells and indicates that the dithio probes disclosed herein can be utilized in methods of labeling and imaging protein disulfides.

Disulfide Proteomics.

Figure 9:
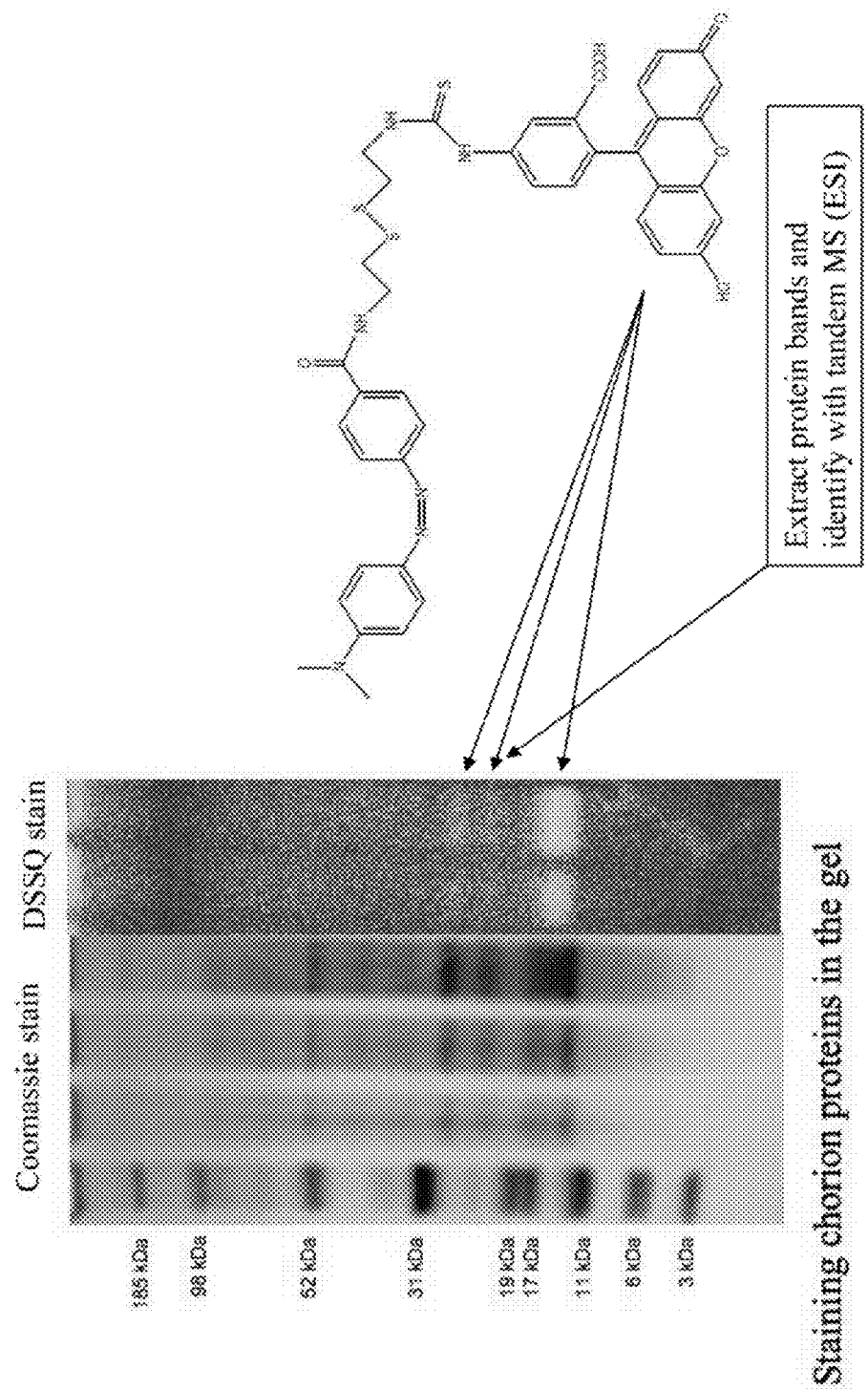
FIG. 9. illustrates a fluorescent image of an SDS PAGE gel of proteins from the labeled chorion in FIG. 8, after labeling protein to produce FSS-protein (right panel). Left panel is the analogous gel, but stained using coomassie. The two bands identified with arrows represent fluorescently tagged proteins (FSS-protein) that were extracted and identified using LC-MS/MS (tandem mass spectrometry) in order to identify any thiol-containing protein(s) with potential role(s) in protecting the developing embryo from electrophiles and/or oxidative stress.

If the fluorescence signal observed in FIG. 8B is from disulfide containing proteins, then it should be possible to purify them and identify them using tandem mass spectrometry (MS). In FIG. 9, when the chorion from the embryos is subjected to SDS PAGE separation, then imaged by reading fluorescence signal, it can be seen that there are fluorescently tagged protein (DSS-protein) bands. These bands were cut from the gel and the protein contained therein was extracted and subjected to proteolysis using trypsin. Then, peptides were subjected to LC-MS/MS analysis, where individual peptide fragments are ionized in a mass spectrometer (ESI, in this case), and the mass/charge fragmentation pattern matched against a database of predicted patterns for the proteome in question (in this case, zebrafish). Using this approach, patterns were obtained for the two bands from the gel in FIG. 9 (Bands L and H) (data not shown). In this manner, Band L (21,097 g/mol) was identified as being from the zebrafish homolog of lipovitellin, a lipid binding protein. Likewise, Band H (23,675 g/mol) was identified as being from the zebrafish homolog of C-reactive protein (CRP), which is an important biomarker protein in humans associated with infection, inflammation and tissue damage. When these proteins were subjected to homology modeling analysis, using the Swiss Model Server (data not shown), high quality homology models could be obtained due to high sequence identity with the template proteins (>30% identity). The 3-dimensional protein structure models clearly indicate that both proteins have disulfide groups, consistent with the above conclusion that the fluorescent dithio probes were reacting with disulfide groups on proteins in the chorion. Accordingly, fluorescent dithio probes can be used in dithio proteomics methods. Furthermore, given the broad clinical important of C-reactive protein, and in general of detecting tissue damage, the fluorescent dithio probes may have utility as a clinical diagnostic reagent to identify tissue damage, infection or inflammation. In this regard, it has been noted that C-reactive protein and lipid transport proteins, in humans, may play a role in lipid transport and tissue damage.

Summary.

The results illustrate that there is utility in tethering fluorescein or other fluorophores to aliphatic systems like peptides (e.g., fluorescein-S—S-peptide).

If will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

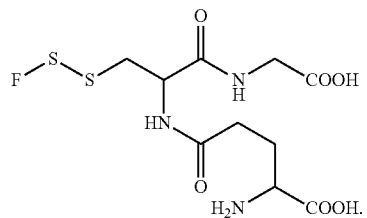 [SMILES: NC(CCC(=O)NC(CSSF)C(=O)NCC(=O)O)C(=O)O]

The invention claimed is:

1. A method for detecting a dithio-containing protein, the method comprising:
   (A) reacting the dithio-containing protein with a dithio-reagent having a formula F—S—S—P to form a reaction product, wherein F comprises a quenched fluorophore and P comprises a peptide and the reaction product comprises the fluorophore and the fluorophore is dequenched in the reaction product; and
   (B) detecting the reaction product via detecting an increase in fluorescence from the dequenched fluorophore.

2. The method of claim 1, wherein the dithio-reagent has a formula: